United States Patent [19]

Kim et al.

[11] Patent Number: 5,998,181
[45] Date of Patent: Dec. 7, 1999

[54] **FERMENTATION PROCESS FOR PREPARING XYLITOL USING *CANDIDA TROPICALIS***

[75] Inventors: Sang Yong Kim, Kyonggi; Deok Kun Oh, Chonbuk; Soo Ryun Jung, Seoul, all of Rep. of Korea

[73] Assignee: Bolak Co., Ltd., Kyunggi-Do, Rep. of Korea

[21] Appl. No.: 09/042,006

[22] Filed: Mar. 13, 1998

[30] Foreign Application Priority Data

Mar. 21, 1997 [KR] Rep. of Korea ............... 97-9717

[51] Int. Cl.[6] ............... C12P 7/18; C12P 19/02; C12N 1/20
[52] U.S. Cl. ............... 435/158; 435/105; 435/255.4; 435/254.22; 435/922
[58] Field of Search ............... 435/105, 155, 435/158, 255.4, 254.22, 924

[56] References Cited

U.S. PATENT DOCUMENTS 5,081,026  1/1992  Heikkilä et al. ............... 435/158
5,686,277  11/1997  Kim et al. ............... 435/158

OTHER PUBLICATIONS

Yahashi et al, J. Ferment. Bioengineer. 81(2):148–152 (1996).
Hontsu et al, Biotechnol. Bioengineer. 40:1085–1091 (1992).
Chemical Abstracts 128(3):20400v (1998).
Chemical Abstracts 127(12):160602s (1997).
N.–J. Cao, et al., *App. Biochem. and Biotech.*, 45/46; 1994, pp. 515–519.
M.G.A. Felipe, et al., *J. Basic Microbiol.*, 35:3, 1995, pp. 171–177.
J.C. duPreez, et al., *Biotech. Lett.*, 13:11, 1991, pp. 827–832.
D.–K. Oh, et al., *Biotech. and Bioeng.*, 58:4, May 20 1998, pp. 440–444.

*Primary Examiner*—Francisco Prats
*Attorney, Agent, or Firm*—Kenyon & Kenyon

[57] ABSTRACT

The present invention relates to a fermentation process for preparing xylitol with high productivity and high yield using a novel strain of *Candida tropicalis*, more specifically, for preparing xylitol under optimal fermentation conditions for maximum xylitol production by optimizing the composition of medium containing xylose and the environmental conditions of culture such as pH, temperature and DO concentration.

2 Claims, No Drawings

FERMENTATION PROCESS FOR PREPARING XYLITOL USING *CANDIDA TROPICALIS*

BACKGROUND OF THE INVENTION

1. Field of the Invention

The present invention relates to a fermentation process for preparing xylitol with high productivity and high yield using a novel strain of *Candida tropicalis*, more specifically, for preparing xylitol under optimal fermentation conditions for maximum xylitol production by optimizing the composition of medium containing xylose and the environmental conditions of culture such as pH, temperature and DO concentration.

2. Description of Prior Art

Xylitol (Xylo-pentane-1,2,3,4,5 pentol) is a naturally occurring five-carbon sugar alcohol that is present in small quantities in a wide variety of fruits, vegetables, and mushrooms. It can be produced by oxalic acid treatment of plant matters such as jute sticks and beech wood residues. However, only small amount present in natural sources, in compared with the amount of sugar cane and sugar beet, makes its quantitative extraction difficult and uneconomical.

It is also a normal metabolic intermediate of carbohydrate metabolism in mammalian. Xylitol has a number of advantageous natural properties. Xylitol has an anticariogenic property which does not cause acid formation and can promote oral health and caries prevention. Since xylitol does not need insulin to regulate its metabolism, it may be used also as a sugar substitute for the treatment of diabetes. Because its metabolism does not involve glucose-6-phosphate dehydrogenase, it is also an ideal sweetner for the person who has the deficiency of glucose-6-phosphate dehydrogenase.

On industrial scale, xylitol is produced through the chemical reduction of xylose derived from hemicellulose hydrolysates of birch wood or other xylose rich materials. As the hemicellulosic fraction of these raw materials contains polymers of other sugars, the process includes extensive purification and separation steps to remove those by-products from xylose or xylitol. The yield of xylitol is about 50~60%. Therefore, xylitol is an expensive product. Since the production of xylitol by the chemical method has been found to be expensive due to its difficult separation and purification steps, it is worthwhile to explore an alternative method for the effective production of xylitol using microorganisms.

To overcome such drawbacks of chemical preparation method, the biological fermentation process for preparing xylitol has been researched. The fermentation process for preparing xylitol using yeast speices from the medium containing xylose or hemicellulose hydrolysate having xylose has been disclosed. Especially, *Candida blankii*, *Candida guilliermondii*, *Candida tropicalis*, *Candida utilis*, *Saccharomyces bailii*, *Saccharomyces rouxii*, *Saccharomyces uvarium* and *Saccharomyces pombe* have been known as the microorganism producing xylitol. However, xylitol production is not quite desirable due to its slow production rate.

To improve the yield and productivity of xylitol, a high xylitol producing yeast in the present invention is isolated from the sludge of xylose manufacturing factory, and then identified as *Candida tropicalis*. The fermentation conditions are optimized using this strain for maximum xylitol production.

SUMMARY OF THE INVENTION

The object of the present invention is to provide novel cells of *Candida tropicalis*, which were deposited to Korean Culture Center of Microorganism with accession number KCCM-10122 on Feb. 20, 1998 under Budapest treaty, for preparing xylitol with high productivity and high yield.

The other object of the present invention is to provide the optimal fermentation process for maximum production of xylitol using a novel strain of *Candida tropicalis* deposited to Korean Culture Center of Microorganism with accession number KCCM-10122 comprising the steps of:

i) fermenting xylose medium with cells by controlling following fermentation conditions;
  a) composition of medium for maximum production of xylitol consists of 5~20(w/v)% of xylose, 0.2~1.0 (w/v)% of glucose, 0.2~2.0(w/v)% of yeast extract, 0.2~2.0(w/v)% of $(NH_4)_2SO_4$, 0.2~2.0%(w/v)% of $KH_2PO_4$, 0.01~0.2(w/v)% of $MgSO_4.7H_2O$;
  b) pH of culture medium is 4.5~5.5;
  c) temperature of cultivation is 27~33° C.;
  d) dissolved oxygen concentration in the medium is 0.1~5.0(w/v) % of air saturation; and
  e) redox (reduction-oxidation) potential in the medium is −50~−150 mV ii) removing cells and other residue from the fermentation medium; and iii) separating and recovering xylitol from the fermentation medium of step ii)

The further object of the present invention is to provide the fermentation process in which xylose and glucose are fed to the medium during the xylitol production phase in following manners comprising:

i) feeding the xylose intermittently into the culture broth; and/or ii) continuously feeding the mixture of xylose and glucose with 20:1~5:1 (w/w).

DETAILED DESCRIPTION OF THE INVENTION

The present invention concerns a method of obtaining xylitol with high yield and high volumetric productivity in *Candida tropicalis* isolated from the sludge of xylose manufacturing factory (Korea Biotech Co., Anyang, Korea). The cells used for the present invention are isolated by following method.

The broth of the sludge of manufacturing xylose is spread and incubated at 28~32° C. on yeast-malt(YM) plate containing 0.8~1.2% of glucose, 0.4~0.6% of peptone, 0.3~0.5% of yeast extract, 0.2~0.4% of malt extract and 1.2~1.8% of agar. Some colonies are selected as fast growing strains. The selected colonies are transferred on the fermentation medium containing 5~15% of xylose, 0.2~0.8% of yeast extract, 0.2~0.8% of $(NH_4)_2SO_4$ and 0.2~0.8% of $KH_2PO_4$ to test xylitol producing activity in shake flask. After incubating at 28~32° C. and 200~240 rpm in 24~36 hours, high xylitol producing strains are selected. The many strains isolated from the sludge of manufacturing xylose are obtained by repeating above selection method more than 10 times. Finally, a highest xylitol producing colony is isolated, and used as a xylitol producing strain in this invention.

The investigations of morphological, cultural, and physiological characteristics are performed according to Kreger-Van Rij method (The yeasts: a taxonomic study Elevier Science Publisher, Amsterdam, 1984) and the isolated strain is identified according to Barnett method (Yeasts: Characteristics and Identification. Cambridge University Press, London, 1983). Physiological characteristics of the isolated strain are as following.

| i) Growth temperature | | | 20° C. + 30° C. | + | 37° C. + 42° C. | – |
|---|---|---|---|---|---|---|
| ii) Growth with | | | 30 % D-glucose | + | 40% D-glucose | + |
| iii) Urea hydrolysis | | | – | | | |
| iv) Starch formation | | | – | | | |
| v) Diazonium blue B formation reaction | | | – | | | |
| vi) Assimilation of nitrate | | | – | | | |
| vii) Spilting of arbutin | | | – | | | |
| viii) Filament | | | + | | | |
| ix) Assimilation of carbon source | | | | | | |
| Glucose | + | Galactose | + | L-Sorbose | – | Sucrose | + |
| Maltose | + | Lactose | – | Trehalose | + | Cellobiose | – |
| Melibiose | – | Raffinose | + | Melezitose | – | Soluble Starch | + |
| D-Xylose | + | L-Arabinose | + | D-Arabinose | – | D-Ribose | – |
| D-Rhamnose | – | Glycerol | + | Erythritol | – | Ribitol | + |
| Galactitol | – | D-Mannitol | + | D-Sorbitol | + | D-Glucitol | – |
| Xylitol | – | Inositol | – | Salicin | – | Inulin | – |
| DL-Lactic acid | – | Succinic acid | + | Citric acid | + | Formic acid | – |
| Ethanol | + | Methanol | – | | | | |

From these results, the isolated strain is identified as *Candida tropicalis*.

These cells are deposited to Korean Culture of Microorganism with accession number KCCM-10122.

The following is fermentation method for producing xylitol using such cells.

Seed Culture

The frozen(–70° C.) cells of *Candida tropicalis* (KCCM-10122) are cultivated in a 250 ml flask containing 40~60 ml of YM medium (0.8~1.2(w/v)% of glucose, 0.4~0.6(w/v)% of pepton, 0.3~0.5(w/v)% of yeast extract and 0.2~0.4(w/v)% of malt extract) at 28~32° C. and 220~260 rpm for 8~16 hours. Then, this seed culture is transferred to a 5L fermentor for producing xylitol in main culture.

Main Culture

The fermentation medium consists of 5~20(w/v)% of xylose, 0.2~2.0(w/v)% of yeast extract, 0.2~2.0(w/v)% of glucose, 0.2~2.0(w/v)% of $(NH_4)_2SO_4$, 0.2~2.0(w/v)% of $KH_2PO_4$, and 0.01~0.2(w/v)% of $MgSO_4.7H_2O$. Fed-batch cultures in the fermentor containing fermentation medium are performed at 28~32° C. and pH 4.5~5.5. Agitation speed is 300~600 rpm. Dissolved oxygen concentration in the medium is 0.1~5.0% of air saturation and redox (reduction-oxidation) potential in the medium is –50~–150 mV, preferably –80~–120 mV, during xylitol producing phase. Fed-batch culture is performed with 2L of initial medium and final volume is 3L by feeding 1.0L of mixture solution of xylose and glucose.

The fermentation process is preferably performed by fed batch process. After xylose is completely consumed in the medium, the amount of xylitol, glucose and xylitol are measured by high performance liquid chromatograpgy (HPLC) equipped with Sugar-Pak I column. Dry cell weight is estimated by using a calibration curve made from relationship between optical density at 600 nm and dry cell weight.

The measured yield of xylitol is 85~98% of the biomass of xylose consumption, and volumetric productivity is 3.0~7.0 g/L-hr, which are increased by 5~15 fold compared with conventional fermentation yield and productivity.

Finally, the fermentation medium is centrifuged for removing cells and other residue, and the supernatant is filtered and dialyzed for obtaining xylitol.

The present invention can be explained more specifically by following examples. However, the scope of the present invention cannot be limited to following examples.

EXAMPLE I

The frozen (–70° C.) cells of *Candida tropicalis* (KCCM-10122) are cultivated in a 250 mL flask containing 40~60 mL YM medium(0.8~1.2(w/v)% of glucose, 0.4~0.6(w/v)% of peptone, 0.3~0.5(w/v)% of yeast extract and 0.2~0.4(w/v)% of malt extract) at 28~32° C. and 220~260 rpm for 8~16 hours, and this seed culture is transferred to a 5L fermentor containing fermentation medium for producing xylitol in main culture. The initial fermentation medium consists of 5~15(w/v)% of xylose, 0.2~1.5(w/v)% of yeast extract, 0.2~2.0(w/v)% of $(NH_4)_2SO_4$, 0.2~2.0(w/v)% of $KH_2PO_4$, 0.01~0.2(w/v)% of $MgSO_4.7H_2O$. Fed-batch culture in the fermentor is performed at 28~32° C. and pH 4.5~5.5. Agitation speed is 300~600 rpm. Dissolved oxygen concentration in the medium is 0.1~5.0% of air saturation and redox (reduction-oxidation) potential in the medium is –50~–150 mV, preferably –80~–120 mV, during xylitol producing phase. Cultures are performed for the period that xylose is completely consumed. Fed-batch culture of xylose is carried out because of the inhibitory effect of high xylose concentration on xylitol production. The volume of fermentor increases from 2 L containing 200 g of xylose to 3 L containing 900 g of xylose by feeding four times of 250 mL containing 150 g of xylose (20, 27, 34, 41 hours).

After 48 hours fermentation, the amount of xylitol is measured by HPLC equipped with Sugar-Pak I column. The obtained xylitol is 240 g/L from 300 g/L of xylose, which corresponds to the xylitol yield from xylose of 80%. Xylitol production rate of the intermittent fed-batch culture is 5.00 g/L-hr.

EXAMPLE II

The frozen (–70° C.) cells of *Candida tropicalis* (KCCM-10122) are cultivated in a 250 mL flask containing 40~60 mL YM medium(0.8~1.2(w/v)% of glucose, 0.4~0.6(w/v)% of peptone, 0.3~0.5(w/v)% of yeast extract and 0.2~0.4(w/v)% of malt extract) at 28~32° C. and 220~260 rpm for 8~16 hours, and this seed culture is transferred to a 5L fermentor containing fermentation medium for producing xylitol in main culture. The fermentation medium consists of 5~15 (w/v)% of xylose, 0.2~1.5(w/v)% of yeast extract, 0.2~2.0 (w/v)% of $(NH_4)SO_4$, 0.2~2.0(w/v)% of $KH_2PO_4$, 0.01~0.2 (w/v)% of $MgSO_4.7H_2O$. Fed-batch culture in the fermentor is performed at 28~32° C. and pH 4.5~5.5. Agitation speed is 300~600 rpm. Dissolved oxygen concentration in the medium is 0.1~5.0% of air saturation and redox (reduction-oxidation) potential in the medium is –50~–150 mV, preferably –80~–120 mV, during xylitol producing phase. Cultures are performed for the period that xylose is completely consumed. Fed-batch culture of xylose is carried out because of the inhibitory effect of high xylose concentration on xylitol production. The volume of fermentor increases from 2 L containing 900 g of xylose by feeding continuously the solution of 1 L containing 700 g of xylose. Xylose feeding is started at residual xylose of 3.0~6.0%.

After 48 hours fermentation, the amount of xylitol is measured by HPLC epuipped with sugar-Pak I column. The obtained xylitol is 255 g/L from 300 g/L of xylose, which corresponds to the xylitol from xylose of 85%. Xylitol production rate of the intermittent fed-batch culture is 5.31 g/L-hr.

EXAMPLE III

The frozen (−70° C.) cells of *Candida tropicalis* (KCCM-10122) are cultivated in a 250-mL flask containing 40~60 mL YM medium (0.8~1.2(w/v)% of glucose, 0.4~0.6(w/v)% of peptone, 0.3~0.5(w/v)% of yeast extract and 0.2~0.4(w/v)% of malt extract) at 28~32° C. and 220~260 rpm for 8~16 hours, and this seed culture is transferred to a 5L fermentor containing fermentation medium for producing xylitol in main culture. The fermentation medium consists of 5~15 (w/v)% of xylose, 0.5~2.0(w/v)% of glucose, 0.2~2.0(w/v)% of yeast extract, 0.2~2.0(w/v)% of $(NH_4)_2SO_4$, 0.2~2.0 (w/v)% of $KH_2PO_4$, 0.01~0.2(w/v)% of $MgSO_4 \cdot 7H_2O$. Fed-batch culture in the fermentor is performed at 28~32° C. and pH 4.5~5.5. Agitation speed is 300~600 rpm. Dissolved oxygen concentration in the medium is 0.1~5.0% of air saturation and redox (reduction-oxidation) potential in the medium is −50~−150 mV, preferably −80~−120 mV, during xylitol producing phase. Cultures are performed for the period that xylose is completely consumed. Fed-batch culture of xylose is carried out because of the inhibitory effect of high xylose concentration on xylitol production. The volume of fermentor increases form 2 L containing 900 g of xylose by feeding continuously the solution of 1 L containing 700 g of xylose and 35 g of glucose. Xylose feeding is started at residual xylose of 3.0~6.0%.

After 48 hours fermentation, the amount of xylitol is measured by HPLC equipped with Sugar-Pak I column. The obtained xylitol is 270 g/L from 300 g/L of xylose, which corresponds to the xylitol yield from xylose of 90%. Xylitol production rate of the continuous fed-batch culture of xylose and glucose is 5.63 g/L-hr.

EXAMPLE IV

The frozen (−70° C.) cells of *Candida tropicalis* (KCCM-10122) are cultivated in a 250 mL flask containing 40~60 mL YM medium (0.8~1.2(w/v)% of glucose, 0.4~0.6(w/v)% of peptone, 0.3~0.5(w/v)% of yeast extract and 0.2~0.4(w/v)% of malt extract) at 28~32° C. and 220~260 rpm for 8~16 hours, and this seed culture is transferred to a 5L fermentor containing fermentation medium for producing xylitol in main culture. The fermentation medium consists of 5~15 (w/v)% of xylose, 0.5~2.0(w/v)% of glucose 0.2~2.0(w/v)% of yeast extract, 0.2~2.0(w/v)% of $(NH_4)_2SO_4$, 0.2~2.0(w/v)% of $KH_2PO_4$, 0.01~0.2(w/v)% of $MgSO_4 \cdot 7H_2O$. Fed-batch culture in the fermentor is performed at 28~32° C. and pH 4.5~5.5. Agitation speed is 300~600 rpm. Dissolved oxygen concentration in the medium is 0.1~5.0% of air saturation and redox (reduction-oxidation) potential in the medium is −50~−150 mV, preferably −80~−120 mV, during xylitol producing phase. Cultures are performed for the period that xylose is completely consumed. Fed-batch culture of xylose is carried out because of the inhibitory effect of high xylose concentration on xylitol production. The volume of fermentor increases from 2 L containing 900 g of xylose by feeding continuously the solution of 1 L containing 700 g of xylose and 100 g of glucose. Xylose feeding is started at residual xylose of 3.0~6.0%.

After 48 hours fermentation, the amount of xylitol is measured by HPLC equipped with Sugar-Pak I column. The obtained xylitol is 290 g/L from 300 g/L of xylose, which corresponds to the xylitol yield from xylose of 97%. Xylitol production rate of the continuous fed-batch culture of xylose and glucose is 6.04 g/L-hr.

EXAMPLE V

The frozen (−70° C.) cells of *Candida tropicalis* (KCCM-10122) are cultivated in a 250 mL flask containing 40~60 mL YM medium (0.8~1.2(w/v)% of glucose, 0.4~0.6(w/v)% of peptone, 0.3~0.5(w/v)% of yeast extract and 0.2~0.4(w/v)% of malt extract) at 28~32° C. and 220~260 rpm for 8~16 hours, and this seed culture is transferred to a 5 L fermentor containing fermentation medium for producing xylitol in main culture. The initial fermentation medium consists of 5~15(w/v)% of xylose, 0.5~2.0(w/v)% of glucose, 0.2~1.5 (w/v)% of yeast extract, 0.2~2.0(w/v)% of $(NH_4)_2SO_4$, 0.2~2.0(w/v)% of $KH_2PO_4$, 0.01~0.2(w/v)% of $MgSO_4 \cdot 7H_2O$. Fed-batch culture in the fermentor is performed at 28~32° C. and pH 4.5~5.5. Agitation speed is 300~600 rpm. Dissolved oxygen concentration in the medium is 0.1~5.0% of air saturation and redox (reduction-oxidation) potential in the medium is −50~−150 mV, preferably −80~−120 mV, during xylitol producing phase. Cultures are performed for the period that xylose is completely consumed. Fed-batch culture of xylose is carried out because of the inhibitory effect of high xylose concentration on xylitol production. The volume of fermentor increases from 2 L containing 900 g of xylose by feeding continuously the solution of 1 L containing 700 g of xylose and 140 g of glucose. Xylose feeding is started at residual xylose of 3.0~6.0%.

After 48 hours fermentation, the amount of xylitol is measured by HPLC equipped with Sugar-Pak I column. The obtained xylitol is 280 g/L from 300 g/L of xylose, which corresponds to the xylitol yield from xylose of 93%. Xylitol production rate of the continuous fed-batch culture of xylose and glucose is 5.83 g/L-hr.

We claim:
1. A fed-batch fermentation process for production of xylitol using a mutant strain of *Candida tropicalis* deposited to Korean Culture Center of Microorganism having accession number KCCM-10122, said process comprising the steps of:

i) growing cells of the mutant strain of *Candida tropicalis* at a temperature of 27~33° C. in medium comprising 5~20 (w/v)% of xylose, 0.2~1.0 (w/v)% of glucose, 0.2~2.0 (w/v)% of yeast extract, 0.2~2.0 (w/v)% of $(NH_4)_2SO_4$, 0.2~2.0 (w/v)% of $K_2HPO_4$, 0.01~0.2 (w/v) of $MgSO_4 \cdot 7H_2O$, wherein said medium has a pH of 4.5~5.5, a redox (reduction-oxidation) potential of −50~−150 mV and a dissolved oxygen concentration of 0.1~5.0(w/v)% of air saturation;

ii) feeding a mixture of xylose and glucose having a volume ratio of 20:1~5:1 (w/w) to the medium during the xylitol production phase of cell growth;

iii) removing cells from the medium; and iv) separating and recovering xylitol from the medium of step (iii).

2. The fermentation process according to claim 1, wherein cells used for fermentation are prepared by cultivating frozen *Candida tropicalis* (KCCM-10122) in YM medium containing 0.8~1.2(w/v)% of glucose, 0.4~0.6(w/v)% of peptone, 0.3~0.5(w/v)% of yeast extract, and 0.2~0.4(w/v)% of malt extract at 27~33° C. for 6~18 hours.

* * * * *